United States Patent [19]

Greear et al.

[11] Patent Number: 5,067,497

[45] Date of Patent: Nov. 26, 1991

[54] INTUBATION DEVICE WITH ADJUSTABLE SUCTION MEANS ABOVE THE CUFF

[75] Inventors: John Greear, Leeds; Marc W. Fournier, Auburn, both of Me.

[73] Assignee: Progressive Medical Design, Inc., Auburn, Me.

[21] Appl. No.: 494,464

[22] Filed: Mar. 16, 1990

[51] Int. Cl.⁵ .................. A61M 16/00; A61M 29/00; A61M 25/00; A62B 9/06
[52] U.S. Cl. .......................... 128/207.15; 128/207.14; 604/96; 604/284
[58] Field of Search ............... 128/207.14, 207.15, 128/207.16, 207.17, 911; 604/96, 284

[56] References Cited

U.S. PATENT DOCUMENTS

| | | | |
|---|---|---|---|
| 3,799,173 | 3/1974 | Kamen | 604/96 |
| 3,905,361 | 9/1975 | Hewson et al. | 604/96 |
| 4,156,428 | 5/1979 | Henkin | 128/207.15 |
| 4,305,392 | 12/1981 | Chester | 128/207.15 |
| 4,327,721 | 5/1982 | Goldin et al. | 128/207.15 |
| 4,407,281 | 10/1983 | Brandt et al. | 128/207.15 |
| 4,584,998 | 4/1986 | McGrail | 128/207.15 |
| 4,607,635 | 8/1986 | Heyden | 128/207.15 |
| 4,632,108 | 12/1986 | Geil | 128/207.15 |
| 4,637,389 | 1/1987 | Heyden | 128/207.15 |
| 4,674,495 | 6/1987 | Orr | 128/207.14 |
| 4,739,756 | 4/1988 | Horn | 128/207.14 |
| 4,804,359 | 2/1989 | Grunwald et al. | 604/284 |
| 4,840,173 | 6/1989 | Porter, III | 128/207.14 |

FOREIGN PATENT DOCUMENTS

| | | | |
|---|---|---|---|
| 1175727 | 10/1984 | Canada | 128/207.14 |
| 2901831 | 7/1979 | Fed. Rep. of Germany | 128/207.14 |
| 3523663 | 1/1987 | Fed. Rep. of Germany | 128/207.15 |
| 0589988 | 2/1978 | U.S.S.R. | 128/207.15 |
| 0825093 | 4/1981 | U.S.S.R. | 128/207.15 |

OTHER PUBLICATIONS

"Tracheotomy and New Tracheal Tube", Arhelger, M. D., *Surgery*, vol. 29, No. 2, pp. 263-266, 1951.

*Primary Examiner*—Edgar S. Burr
*Assistant Examiner*—Kimberly L. Asher
*Attorney, Agent, or Firm*—Sixbey, Friedman, Leedom & Ferguson

[57] ABSTRACT

The present invention relates to a tubular assembly which can be intubated within a body passageway which comprises a main tube body, which permits the passage of fluid in either direction (such as air in the case of an endotracheal tube), an inflatable cuff near the distal end of the main tube body for locating and securing the tubular assembly within a body passageway as well as for sealing the space above the cuff between the main tube body and the body passageway from the body passageway below the cuff, and a suction tube that runs along the main tube body from the proximal end that remains external of the patient during intubation and a point adjacent the inflatable cuff. The suction tube is fixed with the main tube except for an adjustable portion of the suction tube nearest the inflatable cuff that includes the suction tube opening. The adjustment portion of the suction tube is free to move relative to the main tube body such that it is selectively radially adjustable in position to or from the main tube body. Moreover, the adjustable portion of the suction tube is movable by an adjustment balloon positioned between the adjustable portion of the suction tube and the main tube body. Furthermore, the adjustment balloon is selectively inflated or deflated for radially moving the adjustable portion between an innermost position in close proximity to the outer surface of the main tube body, and an outermost position wherein the adjustable portion and suction tube opening are in close proximity to the wall of the body passageway.

23 Claims, 5 Drawing Sheets

INTUBATION DEVICE WITH ADJUSTABLE SUCTION MEANS ABOVE THE CUFF

TECHNICAL FIELD

The present invention relates to endotracheal tubes of the type including an inflatable cuff which is used to securely locate the intubation device within a body passageway such as the respiratory tract. More specifically, the present invention further provides a way of facilitating the suction of secretions and bacteria that collect above the cuff once in place and an adjustable device for positioning the point of suction.

BACKGROUND OF THE INVENTION

Intubation is the placing of a rigid or semi-rigid tube in a body passageway for varying periods of time ranging from a few hours to permanent positioning. Mostly intubation involves the use of such a tube in the respiratory tract to ensure respiration by providing a clear upper airway. Such intubation devices, however, are not limited in use in the respiratory tract, but find application in other body passages wherein a clear pathway is desired. Moreover, such intubation devices find use in various portions of the respiratory tract.

Endotracheal tubes are frequently used for the primary purpose of ensuring that a patient's airway remains clear, which secondarily provides access to the bronchial tree for the aspiration of secretions. However, by the fact that the intubation device is a tube placed within the body passageway, the natural lumen or size thereof is necessarily reduced, although the narrower tube lumen is ensured to be clear. This leads to a specific problem which is brought on by the provision of an inflatable cuff near a distal end of the intubation device which is inflated once the tube is intubated for securely holding the tube in place and for sealing the tube to the body passageway so that all of the air passing to and from the patient's lungs must pass through the tube. The inflated cuff, in position, forms a space above the cuff and between the intubation device and the body passageway within which secretions and bacteria, or the like, will accumulate. Although the accumulation of the secretions is not particularly beneficial, the seal of the inflatable cuff advantageously prevents the accumulated secretions from passing into the patient's lungs so long as the cuff remains fully inflated. However, the problem is that the secretions that build up within this space may also cause harm the patient.

When the intubation device is intubated within the respiratory tract, the tube passes into the trachea through the epiglottis, and as a result the epiglottis cannot then close. Thus, saliva from the mouth can pass and become trapped in the larynx and trachea. Moreover, other secretions that are produced by the body are trapped as well. The large amount of secretions and bacteria that collect in the space above the cuff can be disadvantageously drawn into the patient's lungs during coughing, cuff deflation, or extubation (i.e., tube removal). This not only presents an immediate danger to the patient's ability to breath, but is believed to substantially increase the chance that the patient will develop aspiration pneumonia.

Thus, it has become desirable to find ways for removing the secretions and bacteria that collect above the cuff during the time period of intubation. Typically, such removal includes the application of suction to the above-the-cuff region for the removal of collected secretions. The initial solution was simply to periodically insert a suction catheter along with the intubation device once intubated and sealed by the cuff, to suction out accumulated secretions. As a modification to this procedure, it is presently known to provide an intubation device including an integrally formed suction catheter with an opening in the above-the-cuff region through which periodic or constant suction can be applied for removal of secretions after intubation.

A further modification and example of a combination intubation device with a separate channel to facilitate suction is described in U.S. Pat. No. 4,607,635 to Heyden. The endotracheal tube of Heyden comprises an intubation tube having an inflatable cuff near its distal end, wherein an elongated channel or passageway is provided along the length of the main tube and extends from the proximal end of the main tube to the cuff. Furthermore, the channel is provided with a plurality of ports along its entire length which define various points for suction to be applied along the tube. However, in operation, it is necessary to insert a suction catheter within the channel which when moved along the channel draws secretions into the suction catheter through each of the ports of the channel. The operation of this type of endotracheal tube disadvantageously causes an increase in patient discomfort associated with insertion and removal of the suction catheter as well as an increased tracheal irritation that results from suction being applied along the length of the trachea through the various ports. Additionally, it is necessary to regulate the insertion of the catheter and to control the depth thereof since unintentional overinsertion of the catheter could damage or puncture the cuff.

Although the Heyden '635 endotracheal tube does provide for an adjustment regarding the axial direction of the intubation device and the body passage, it has been found to be inadequate with regard to suctioning of accumulated secretions because it does not provide for any radial displacement just above the cuff. This has been found to be particularly important since the large majority of secretions that accumulate collect near the cuff along the tracheal wall in the region above the cuff. This is caused because of the general tendency of the secretions to flow toward the cuff due to a typical patient's orientation, that is downwardly toward the cuff, and additionally because the inflation of the cuff causes an expansion of the body passageway at the cuff which consequently enlarges the space formed just above the cuff in the radial sense. As a result, most secretions collect in this enlarged area. With the Heyden '635 device, the application of suction near the cuff is limited to the end port of the channel guiding the suction catheter so as to permit suction only very near the tube sidewall of the intubation device. This point of suction has been found to be inadequate in that all of the accumulate secretions cannot be removed. Granted, the inflation or deflation of the cuff will somewhat radially move and position the ports in the channel; however, there can be no radial adjustment once the intubation device is put in place by the inflated cuff, since any attempted movement would defeat the purpose of the cuff in that secretions would pass into the patient's lungs. Thus, the Heyden '635 device is unsuitable for the removal of the large amounts of secretions and bacteria that accumulate in the intubated pathway of a patient, particularly in the region above the cuff nearby the cuff.

A further modification to the above-described Heyden device is disclosed in U.S. Pat. No. 4,637,389 also to Heyden. The purpose of the modified intubation device is to provide a somewhat concealed channel on the intubation device but which functions similarly to the aforementioned Heyden device. Likewise, the channel includes a plurality of ports along the length of the tube and requires the insertion of a suction catheter to remove secretions via each port. The purpose is to protect the suction catheter from the direct contact with the intubated pathway to apparently reduce the aforementioned trauma and discomfort along the tracheal passageway. Once again, such a device is insufficient for effective removal of secretions that accumulate above and near the cuff, since there is no provision of any means to permit the application of suction at radially adjustable positions.

Other devices are available for removal of unwanted substances that may accumulate above the cuff in an intubated passageway of a patient. For example, for removing smoke that results in laser surgery, U.S. Pat. No. 4,632,108 to Geil discloses an endotracheal tube including an opening formed on the exterior of the tube above and adjacent the inflatable cuff at the distal end of the tube. In this case, a lumen is used to connect the opening to a smoke removal tube for removal of accumulated smoke in the region above the cuff. While such is suitable for that purpose, that is smoke removal, such a device need not be provided with the capability to position the opening in a close proximity to the tracheal wall for adequate removal of secretions and bacteria Consequently, there is a need for an endotracheal tube that can effectively remove a large amount of secretions and bacteria that accumulate in the intubated pathway of a patient, and in particular, that accumulate in the region just above the cuff.

SUMMARY OF THE INVENTION

It is therefore a primary object of the present invention to provide a tubular assembly for intubation of a body passageway that overcomes the above-noted deficiencies of the prior art.

It is another object of the present invention to provide a tubular assembly for intubation of a body passageway wherein the tubular assembly is operable to effectively remove substantially all of the undesirable secretions and the like that accumulate around the tubular assembly in the intubated body passageway of a patient.

It is yet another object of the present invention to provide a tubular assembly for intubation of a body passageway including a main tube body, an inflatable cuff, and a suction tube with an opening disposed above and adjacent the inflatable cuff, wherein the suction tube includes an adjustable portion at the end of the suction tube nearest the inflatable cuff which is selectively positionable such that the undesirable secretions that accumulate in the intubated passageway above the cuff can be easily and effectively removed.

It is yet another object of the present invention to provide a tubular assembly for intubation of a body passageway including a main tube body, an inflatable cuff, and a suction tube having an adjustable end portion adjacent the inflatable cuff for selectively radially positioning the open end of the suction tube along the inflatable cuff to move the open end from adjacent the main tube body to a point very near the body passageway.

It is still another object of the present invention to provide a tubular assembly for intubation of a body passageway including a suction tube with an end portion thereof adjustably positioned between the main tube body and the inner surface of the body passageway which also is operable such that a probe or other instrument can be inserted into the suction tube and adjustably positioned between the main tube body and the body passageway.

It is yet another object of the present invention to provide a tubular assembly for intubation in a body passageway including a main tube body and a suction tube having an adjustably positionable end portion, wherein the suction tube can be utilized for lavaging (i.e., washing) the body passageway by supplying a lavaging fluid through the suction tube which can thereafter be suctioned out. Moreover, the supply of fluid and suction is advantageously provided from a location completely external from the patient at the proximal end of the tubular assembly.

The present invention achieves the above objects as well as others by providing a tubular assembly which can be intubated within a body passageway which comprises a main tube body, which permits the passage of fluid in either direction (such as air in the case of an endotracheal tube), an inflatable cuff near the distal end of the main tube body for locating and securing the tubular assembly within a body passageway as well as for sealing the space above the cuff between the main tube body and the body passageway from the body passageway below the cuff, and a suction tube that runs along the main tube body from the proximal end that remains external of the patient during intubation and a point adjacent the inflatable cuff. The suction tube is fixed with the main tube except for an adjustable portion of the suction tube nearest the inflatable cuff that includes the suction tube opening. The adjustment portion of the suction tube is free to move relative to the main tube body such that it is movably positionable radially from the main tube body. Moreover, the adjustable portion of the suction tube is selectively adjustably radially positionable with respect to the main tube body by an adjustment balloon positioned between the adjustable portion of the suction tube and the main tube body. Furthermore, the adjustment balloon is fluidically in communication with a means for inflating or deflating the adjustment balloon for selectively positioning the adjustable portion of the suction tube radially with respect to the main tube body. Preferably, the adjustment balloon as well as the inflatable cuff are inflated and deflated by way of passages passing within the wall defining the main tube body. Thus, the adjustable portion of the suction tube can be positioned at an innermost position in close proximity to the outer surface of the main tube body, and an outermost position wherein the adjustable portion and suction tube opening are in close proximity to the wall of the body passageway.

In a preferred embodiment, an endotracheal tube device comprises an elongate main tube body defined by a tubular wall having an outer wall surface and an inner wall surface. The main tube body having a distal end to be disposed within the body passageway during intubation and a proximal end to be disposed outside of the body passageway during intubation, wherein the inner wall surface of the main tube body defines a primary lumen extending from the proximal end to the distal end thereof. An inflatable cuff is mounted on the outer wall surface of the main tube body adjacent the distal end, with the inflatable cuff being of sufficient size and resiliency to form a sealing relationship between the outer surface of the main tube body and the body passageway during intubation. A secondary lumen is provided with the primary lumen between the proximal end of the main tube body and the inflatable cuff, wherein the secondary lumen has an adjustable end portion at the end adjacent the inflatable cuff, and an adjustment means is provided between the adjustable end portion and the main tube body for causing movement of the adjustable end portion between an innermost position adjacent the main tube body and an outermost position very close to the body passageway. In one embodiment, the secondary lumen is provided by a suction tube provided on the outer wall surface of the main tube body, with the adjustable end portion completely free of the main tube body. In a second embodiment, the secondary lumen comprises a suction tube formed internal of the primary lumen on the inner wall of the main tube body with the adjustable end portion extending out from the main tube body and completely free of the main tube body. Finally, in a third embodiment, the secondary lumen is a suction tube provided partially within and partially outside of the main tube body with the adjustable end portion completely free of the main tube body. In any case, the main tube body and suction tube can be made integrally with one another or by adhering separately formed elements together. Moreover, the suction tube and main tube body are formed of flexible material which is sufficiently stiff such that the suction tube and main tube body will not collapse during operation.

These and further objects, features and advantages of the present invention will become more apparent from the following description when taken in connection with the accompanying drawings which show, for purposes of illustration only, several embodiments in accordance with the present invention.

DETAILED DESCRIPTION OF THE PREFERRED EMBODIMENTS

Figure 1:
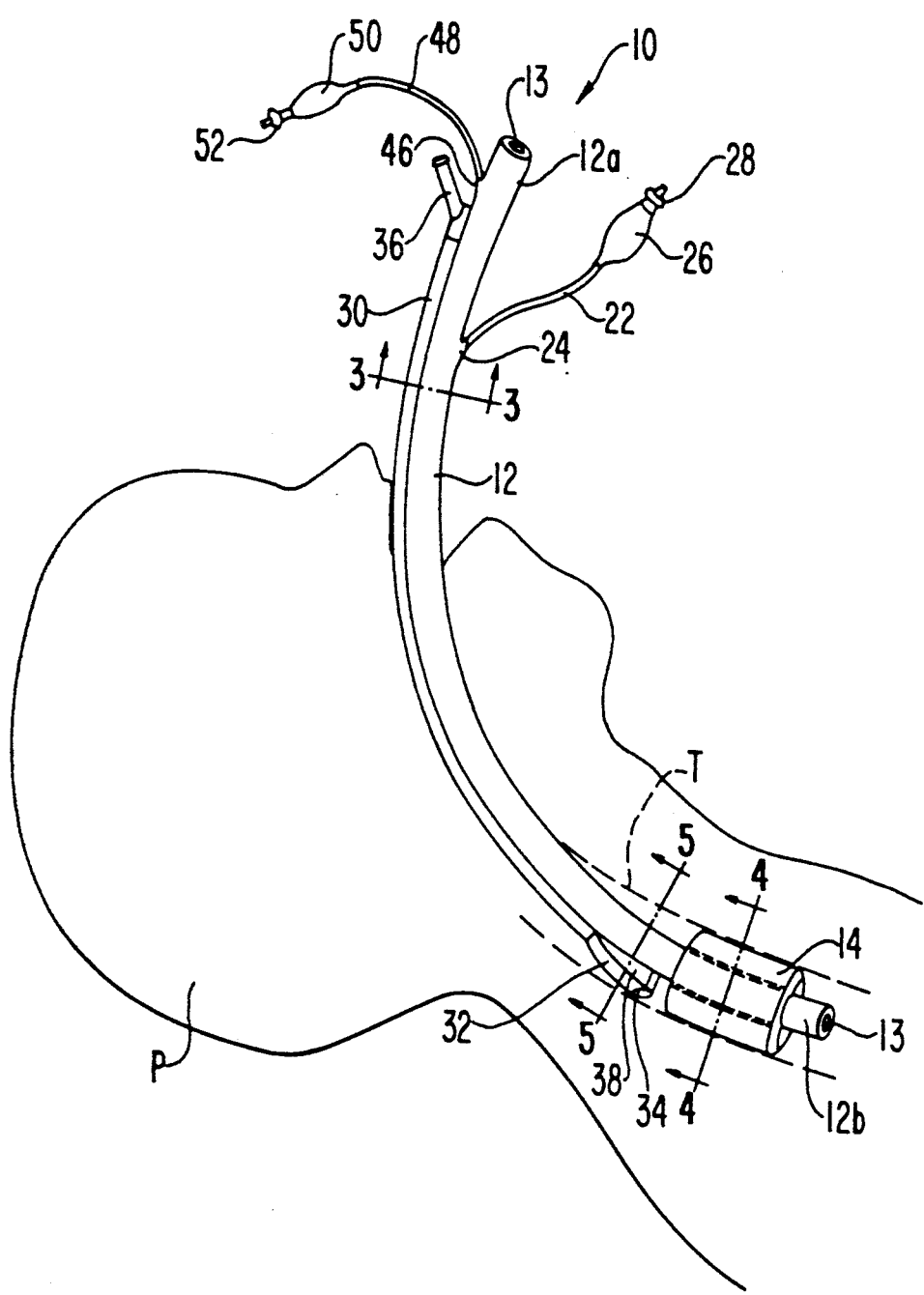
FIG. 1 is a perspective view of an endotracheal tube with an adjustable suction means just above the cuff formed in accordance with a preferred embodiment of the present invention, illustrated with the tubular assembly intubated within a body passageway of a patient, and with the suction tube in a radial extended position.
Figure 2:
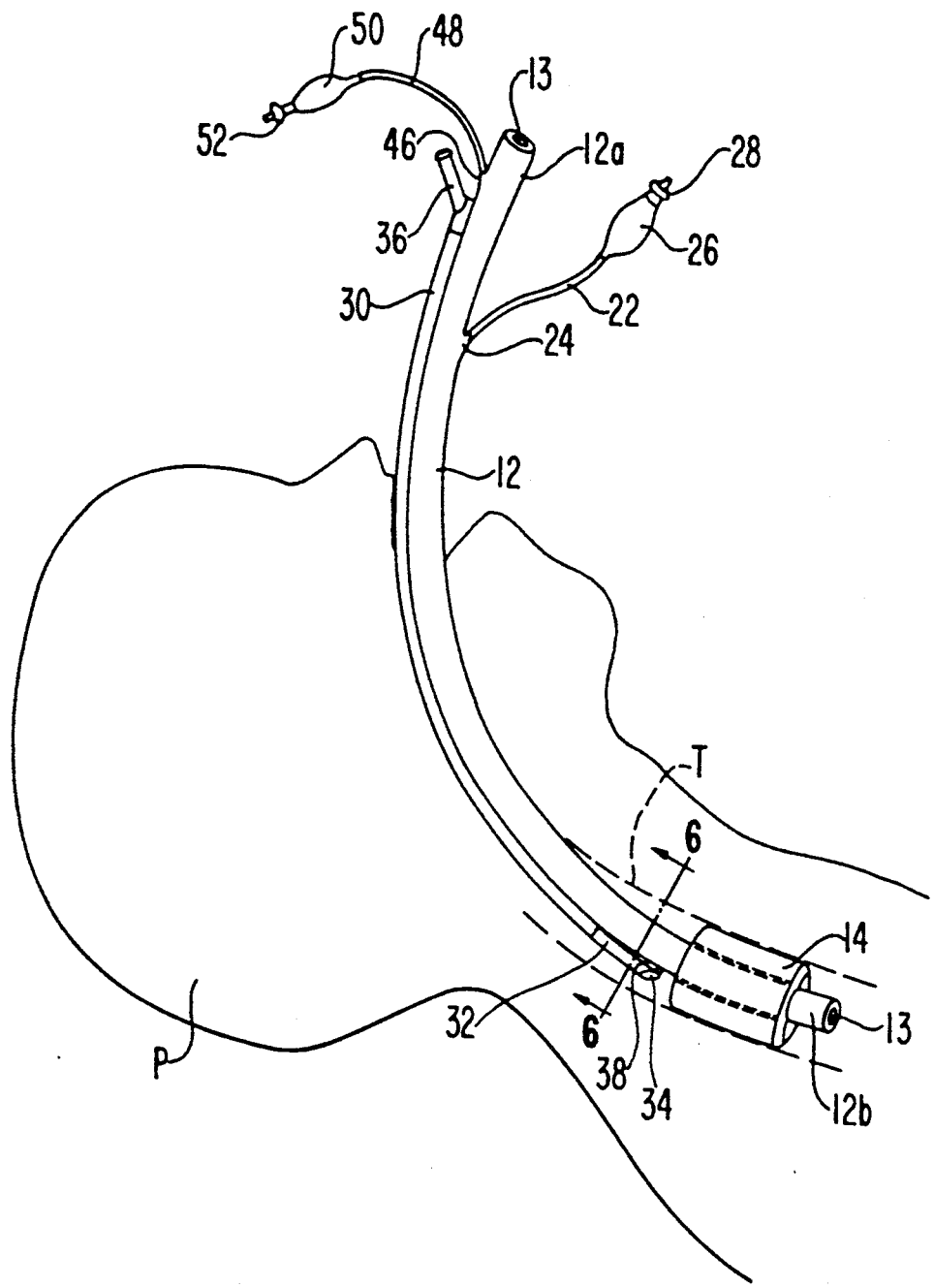
FIG. 2 is a perspective view similar to FIG. 1 of the tubular assembly intubated within a patient, wherein the suction tube just above the cuff lies in its non extended radial innermost position.

With reference now to the several Figures and in particular to FIGS. 1 and 2, wherein like numerals represent like parts throughout each of the several Figures, a tubular assembly 10 is illustrated in accordance with a preferred embodiment. The tubular assembly 10 includes a main tube body 12, which defines therein a primary lumen 13 defined by the inner wall of the main tube body 12 that runs from a proximal end 12a to a distal end 12b.

As illustrated in FIG. 1, the tubular assembly 10 is positioned in its inserted or intubated position within a patient P passing through the patient's mouth and into a body passageway, which as illustrated represents the trachea T of the patient P. The intubation of such a tubular assembly 10 within the trachea T is a preferred use of the present invention; namely, as an endotracheal tube. It is, of course, understood that such tubular assemblies for intubation in a body passageway can be used in other body passageways wherein it is desirable to maintain a clear fluid path between a point internal and a point external of the patient. When used as an endotracheal tube, the device facilitates clear airflow to and from the patient's lungs through the primary lumen 13. Although the primary lumen 13 is small compared to the natural lumen defined through the trachea T, the primary lumen 13 ensures air passage through a clear lumen. Note that the scale shown in the Figures exaggerates the size of the trachea as opposed to the size of the primary lumen 13 for the sake of clarity of the device.

At the distal end 12b of the main tube body 12, an inflatable cuff 14 is provided external to the main tube body 12, that is attached around the circumference of the outer wall of the main tube body 12. The inflatable cuff 14 is formed of an elastomeric rubber or plastic which is expanded or deflated depending on fluid supplied to the inflatable cuff 14. The construction of the inflatable cuff 14 is conventionally known and common to such tracheal tubes.

Figure 3:
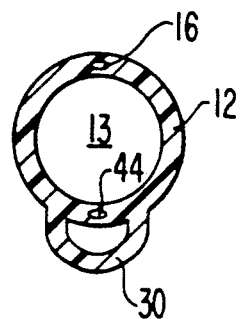
FIG. 3 is an enlarged cross section taken along line 3—3 in FIG. 1.
Figure 4:
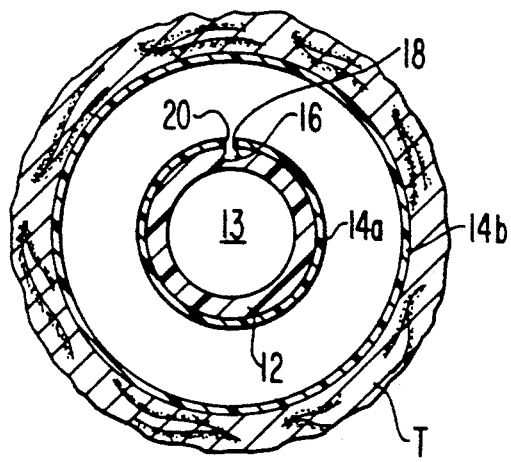
FIG. 4 is an enlarged cross section taken along lone 4—4 in FIG. 1.

With reference now to FIGS. 3 and 4, the inflation circuit for inflating or permitting deflation of the inflatable cuff 14 is shown. Particularly, an inflation conduit 16 is shown that runs within the wall defining the main tube body 12 and along the axial length thereof. The inflation conduit 16 opens into the interior of the inflatable cuff 14 between an inner wall 14a and an outer wall 14b through a port 18 that opens through the external wall of the main tube body 12 and a corresponding port 20 entirely through the inner wall 14a of the inflatable cuff 14. Preferably, near the proximal end 12a of the main tube body 12 an inflation tube 22 is provided that fluidically connects with the inflation conduit 16 at point 24, and includes at its other end a pilot balloon assembly 26 that is used for the inflation of the main tube body 12 in a known manner, such as by a syringe. Additionally, a check valve 28 is provided at the end of the pilot balloon 26 through which fluid can be released.

The inflatable cuff 14 is used to provide a seal between the main tube body 12 and the inner wall of the body passageway into which the tubular assembly 10 is intubated, such as the trachea T shown in FIG. 1. The seal caused by the inflatable cuff 14 ensures that all air passing to and from the patient lungs must pass through the primary lumen 13. Moreover, the seal prevents the flow or seepage of those secretions, bacteria, or the like that tend to accumulate within the trachea T in the space defined above the inflatable cuff 14 outside of the tubular assembly 10. However, and as a specific problem solved by the present invention, if the accumulated secretions are permitted to remain above the inflatable cuff 14, then it becomes possible that the secretions could pass into the patient's lungs during coughing or cuff deflation before extubation. Thus, the patient could be harmed by the secretions in the lungs, as emphasized above in the Background of the Invention.

As can be seen in FIG. 1, any secretions that would be produced above the inflatable cuff 14 while the tubular assembly 10 is intubated within the patient P will tend to accumulate in the space just above the inflatable cuff 14, and more specifically, at the lower side of the main tube body 12 along the tracheal wall just above the inflatable cuff 14. A main component of the secretions which accumulate in this area come from saliva that passes from the mouth of the patient P through the epiglottis, which is maintained opened by the fact that the tube passes therethrough, and into the larynx and trachea T of the patient P. Moreover, other secretions and bacteria may similarly accumulate there as well.

In order then to either periodically or constantly remove these secretions that accumulate above the cuff between the main tube body 12 and the inner wall of the trachea T, a suction tube 30 is provided that extends along the main tube body 12 from near the proximal end 12a to a point just above the inflatable cuff 14. Moreover, the suction tube 30 is preferably fixed with the main tube body 12 along the majority of its length, except for an adjustable free end portion 32 which is not directly connected to the main tube body 12. The adjustable free end portion 32 also includes a suction opening 34 at the end nearest the inflatable cuff 14. At the opposite end of the suction tube 30, a suction hose adapter 36 is preferably provided, which facilitates the connection of the suction tube 30 to a suction source (not shown). The suction hose adapter 36 can be a conventional L-adapter or other angled adapter. Thus, by the combination of the suction tube 30, adjustable free end portion 32, suction opening 34, suction hose adapter 36, and a suction source, the secretions that accumulate in the space above the inflatable cuff 14 between the main tube body 12 and the trachea T can be periodically or constantly removed.

Figure 5:
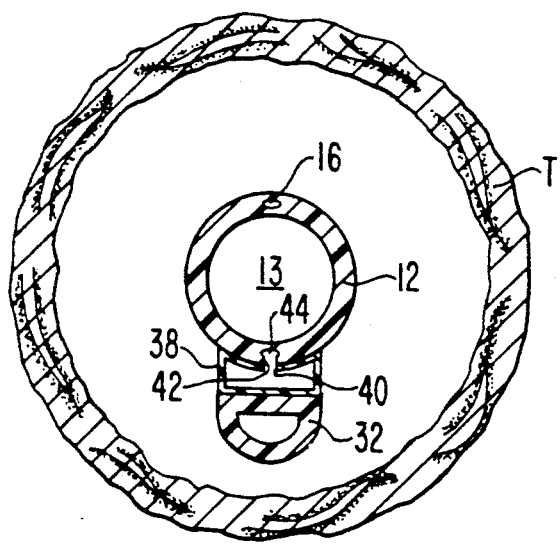
FIG. 5 is an enlarged cross section taken along line 5—5 in FIG. 1.
Figure 6:
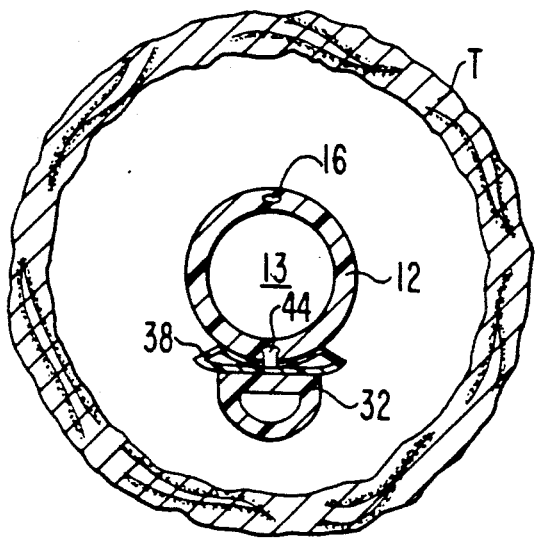
FIG. 6 is an enlarged cross section taken along line 6—6 in FIG. 2.

Located between the adjustable free end portion 32 of the suction tube 30 and the external surface of the main tube body 12 is provided a radial adjustment means or actuating means comprising an adjustment balloon 38. The adjustment balloon 38 is made of an elastomeric rubber or plastic similar to that of the inflatable cuff 14 so as to be inflatable and deflatable such that the radial position of the adjustable free end portion 32 of the suction tube 30 can be moved to and away from the external surface of the main tube body 12. The details of the adjustment balloon are best shown in FIGS. 3, 5 and 6. The adjustment balloon 38 is adhered to both the adjustable free end portion 32 and the external surface of the main tube body 12, and forms a sealed enclosure except that a port 40 passes through an inner wall of the adjustment balloon 38 and the port 40 communicates with a port 42 passing through a portion of the wall of the main tube body 12 and into a second inflation conduit 44. Likewise, as with the inflation conduit 16, the second inflation conduit 44 runs within the wall of the main tube body 12 from the adjustment balloon 38 to a connection point 46 where another inflation tube 48 connects therewith. Also, a second pilot balloon 50 having a check valve at 52 is connected at the other end of the inflation tube 48 so that fluid can be supplied or released for inflation or deflation of the adjustment balloon 38. It is understood that all connection points and ends of the inflation conduits 16 and 44 are appropriately sealed so that proper fluid communication is established.

Referring now to FIG. 2, the tubular assembly 10 is shown intubated within a patient P in the patient's trachea T, similar to FIG. 1. However, in FIG. 2, the adjustable free end portion 32 of the suction tube 30 is shown in its innermost position, wherein the adjustment balloon is fully collapsed. FIG. 6 shows a cross-section through the main tube body 12, adjustable free end portion 32, and the adjustment balloon 38 in this collapsed position. Referring back again to FIG. 1, the adjustable free end portion 32 of the suction tube 30 is illustrated in its outermost or fully extended position of the adjustment balloon 38. In this position, the suction opening 34 is located most nearly the interior surface of the trachea T into which the tubular assembly 10 is intubated, and yet very close to the inflatable cuff 14. FIG. 5 shows a cross-section taken through the main tube body 12, adjustable free end portion 32, and the adjustment balloon 38 in this extended position.

By this selective positioning of the adjustable free end portion 32 of the suction tube 30 and thus the location of the suction opening 34, the suction of accumulated secretions is advantageously improved. This is because almost all of the accumulated secretions can be removed. By advantageously positioning the suction opening 34 very near the tracheal wall and the inflatable cuff 14 an optimal point for suction to be applied is established. Also by removing mostly all of the secretions, less irritation of the tracheal wall results. Moreover, note that the suction tube 30 is provided on the outer curvature of the main tube body 12 so as to be positioned at the lower side of the main tube body 12 just above the inflatable cuff 14. It is preferable that the suction opening 34 be as close as possible to the inflatable cuff 14 without fear of the side of the cuff 14 affecting the suction of secretions into the suction opening 34. However, it is noted that certain situations may not require the extension of the adjustable free end portion 32 to its radial outermost position, and the present invention can be used to select the best radial position desired.

As seen in FIG. 3, it is preferable that the main tube body 12 and the suction tube 30 are formed integral with one another and with inflation conduits 16 and 44 formed therein. Such an integral piece can be easily made by an extrusion process. It is, however, contemplated that the main tube body 12 and the suction tube 30 can be made of separate components which are adhered together by adhesive or heat or both. In either case, it is fundamentally important to the present invention that the adjustable free end portion 32 can move freely with respect to the main tube body 12. The length of the adjustable free end portion 32 is not critical, except that the length must be at a minimum sufficient to permit the suction opening 34 to move from a point adjacent the exterior surface of the main tube body 12 to a point very near the interior surface of the body passageway intended to be intubated. Moreover, in order to provide the adjustable free end portion 32, the free end 32 may be simply formed by splitting off a portion of an integrally formed suction tube from the main tube body at the end nearest the inflatable cuff 14. However, it is preferable that the adjustable free end portion is provided separately and is further provided with an adapter that inserts within the suction tube 30 by way of an opening or slit providing access to the suction tube 30. Preferably, the suction tube would be removed in that region. It is also contemplated that any other convenient or conventional means for connecting an adjustable free end portion 32 to the suction tube 30 can be used.

In operation of the tubular assembly 10, the device must first be intubated within a body passageway by inserting the device into the body passageway with the inflatable cuff 14 deflated and preferably with the adjustment balloon 38 also deflated. Thereafter, the inflatable cuff 14 is inflated by supplying fluid into the pilot balloon 26 for expansion of the inflatable cuff 14 and sealing between the main tube body 12 and the body passageway. Such a position is shown in FIG. 2. Then, either immediately or after a period allowing secretions to accumulate, the adjustable free end portion 32 and thus the suction opening 34 can be moved from its innermost position adjacent the main tube body 12 to a radially selected new position away from the main tube body 12. Moreover, the extent to which the adjustable free end portion 32 is radially displaced, depends on the particular situation. It may be required to move the adjustable free end portion 32 only a radial short distance, or the entire radial distance necessary to position the suction opening 34 just adjacent to the interior wall of the intubated body passageway. In order to move the adjustable free end portion 32, adjustment balloon 38 is inflated or deflated by way of the supply of pressurized fluid or release thereof from pilot balloon 50 and check valve assembly 52. Thus, all of the inflation and deflation operation is controlled from a point near the proximal end of the main tube body completely external of the patient P.

In another use of the present invention, the suction tube 30 can be used as a guide conduit into which a catheter, supply tube or probe can be inserted. More specifically, a supply tube can be inserted within the suction tube 30 for unclogging the suction tube 30 periodically, or lavaging the internal area of the body passageway. Moreover, once the supply of any lavaging fluid or the like is completed, the fluid as well as secretions can be removed by applying suction to the suction tube 30. Furthermore, it is apparent that no matter whether suction is applied or a fluid is provided, such a suction source or fluid supply can be readily attached to the suction tube 30 by way of the suction tube adapter 36. If it is desirable to insert a catheter or probe, the suction tube adapter 36 can be removed for access, and the adjustment balloon 38 can be used to radially position the inserted end of the catheter or probe.

Figure 7:
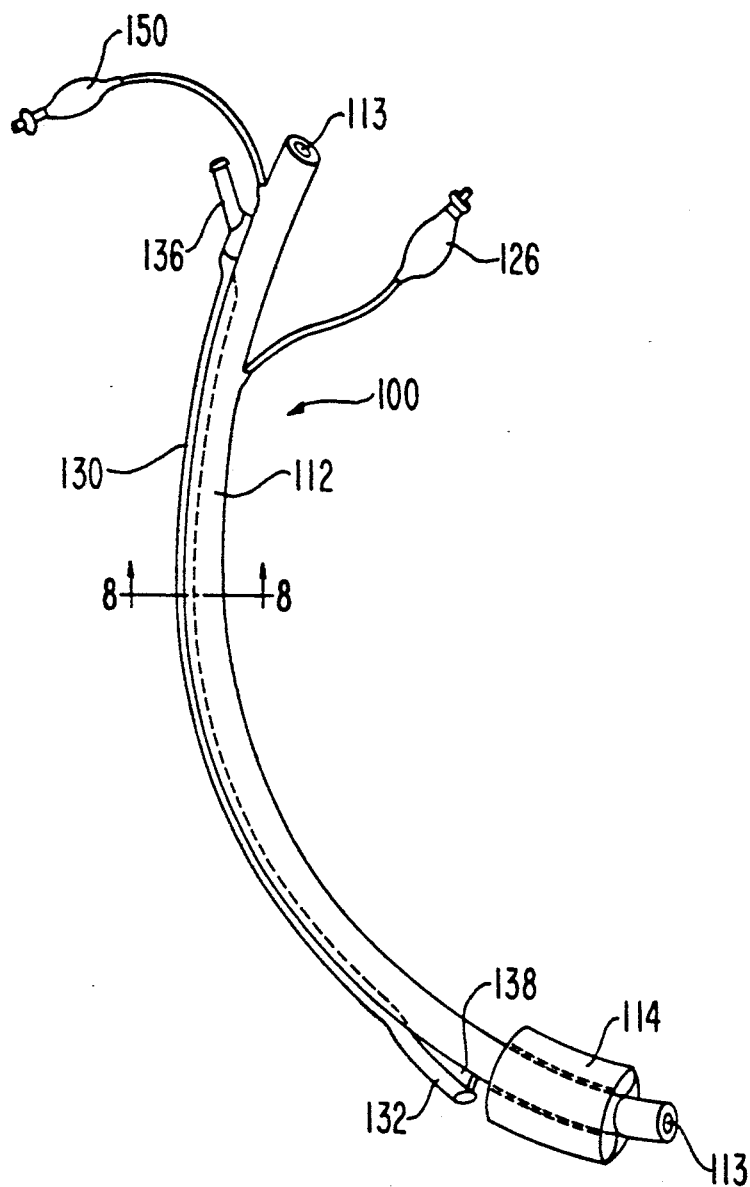
FIG. 7 is a perspective view of another embodiment of an endotracheal tube assembly formed in accordance with the present invention.
Figure 8:
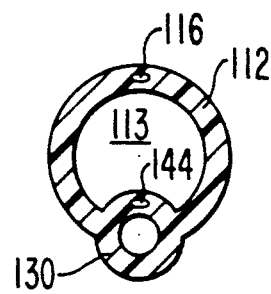
FIG. 8 is an enlarged cross section taken along line 8—8 in FIG. 7.

Referring now to FIGS. 7 and 8, a second embodiment designed in accordance with the present invention is illustrated. In the second embodiment, the tubular assembly 100 functions in the same way as that outlined above with respect to the first embodiment of tubular assembly 10. The main difference is in the cross-section of the tube, as shown in FIG. 8 which is taken along line 8—8 in FIG. 7. The design according to this embodiment permits the suction tube 130 to be somewhat inset, preferably halfway, within the main tube body 112. By this construction, there is a smaller overall diameter for tube assembly 100, which facilitates easier insertion for intubation within a patient. Moreover, the tubular device 100 is preferably formed with the main tube body 112 and the suction tube 130 integral with one another and with the adjustable free end portion 132 formed as a component connected with the suction tube 130. More specifically, the adjustable free end portion 132 as well as the suction hose adapter 136 are provided with an insertable portion that slides within the suction tube 130 by way of an opening or slit cut within the suction tube 130 as formed. The insertion of course must be a sealed connection allowing fluid communication without leakage. The device further includes an inflatable cuff 114, an inflatable adjustment balloon 138, first and second pilot balloons 126 and 150, respectively, for the inflatable cuff 114 and the adjustment balloon 138, respectively, and first and second fluid conduits 116 and 144, respectively. A primary lumen 113 is defined through the main tube body 112 as somewhat reduced with respect to the FIGS. 1-6 embodiment in cross-section.

Figure 9:
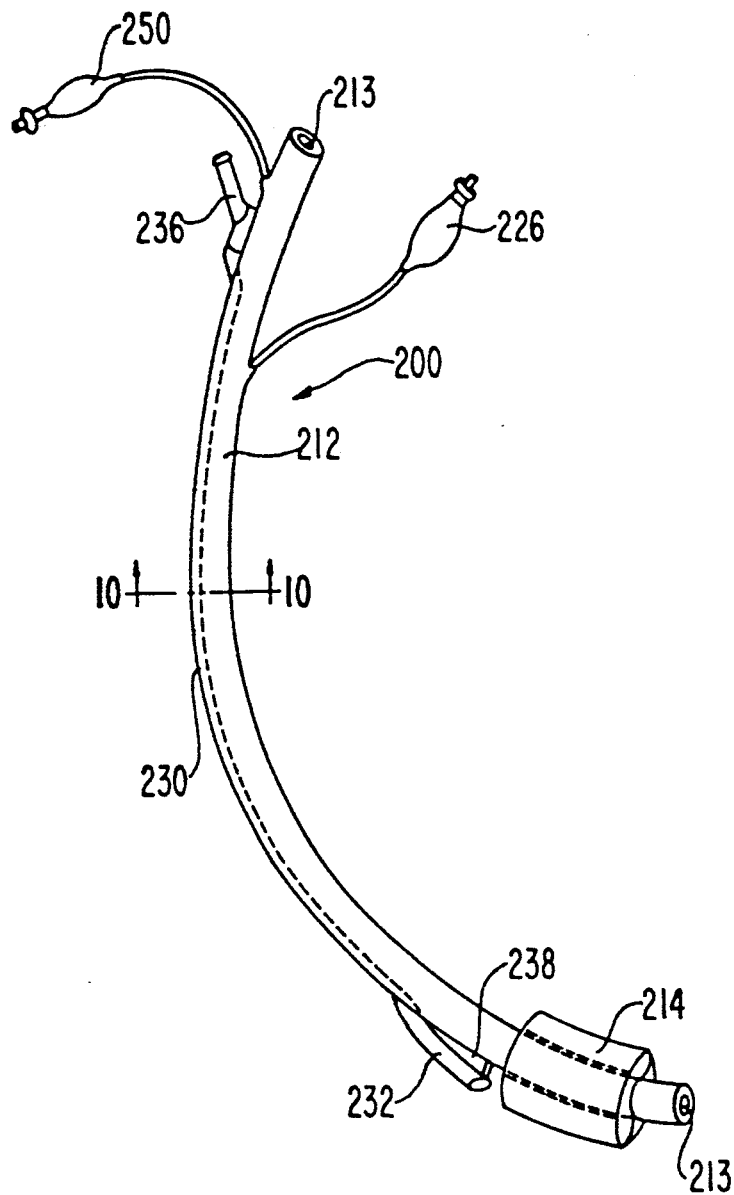
FIG. 9 is a perspective view of yet another embodiment of an endotracheal tube assembly formed in accordance with the present invention.
Figure 10:
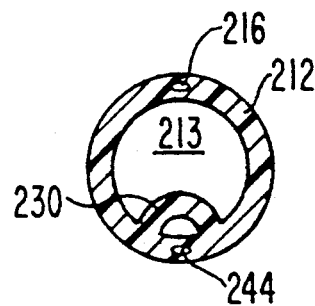
FIG. 10 is a cross section taken along line 10—10 in FIG. 9.

Now, with reference to FIGS. 9 and 10, a third embodiment formed in accordance with the present invention is illustrated which also functions similarly as both previously described embodiments. The basic difference in the third embodiment is the incorporation of the suction tube 230 within the area defined by the circumference of the inner surface of the main tube body 212. The result is that the combined diameter of the tubular assembly 210 is reduced even further such that the entire diameter is defined by the diameter of the main tube body 212. Similarly, as with the FIGS. 7 and 8 embodiment, the adjustable free end portion 232 and the suction hose 236 will include adapters permitting insertion in a sealing manner within the suction tube 230 for fluid connection therebetween. The tubular assembly 210 further includes an inflatable cuff 214, an adjustment balloon 238, inflation conduits 216 and 244 for the inflatable cuff 214 and adjustment balloon 238, respectively, and pilot balloons 226 and 250 for the inflatable cuff 214 and adjustment balloon 238, respectively. The main tube body 212 likewise defines a primary lumen 213, which is somewhat reduced as compared to the FIGS. 1-6 embodiment and the FIGS. 7 and 8 embodiment in that the suction tube 230 takes up a portion of this volume.

It is further understood that the tubular assemblies 10, 100 and 200 are composed of a material that is semi-rigid, that is somewhat resilient, but sufficiently stiff to ensure that the primary lumen 13, 113 or 213, and the suction tube 30, 130 or 230 remain uncollapsed and clear throughout their use. Particularly, it is important that the material not collapse around the suction tube when suction is applied thereto, such as would result if the material were too flexible wherein the walls may be closed together one on another.

Moreover, it is understood that the above described embodiments may be modified further with obvious variations that still fall within the scope of the present invention. Specifically, the device can be designed to work specifically in different body passageways, or in different positions or portions of a particular body passageway, such as the trachea. Additionally, it may be possible to include an axial adjustment for the point of application of suction, such as by including plural ports along the suction tube, which may be arranged to be used as they are or in combination with an insertable suction catheter. However, such a device would advantageously still allow the radial repositioning of the end of the suction catheter by selectively moving the adjustable free end and the suction opening thereof. Furthermore, when considering the use in other body passageways, it may be desirable to locate the suction tube at a different peripheral location with respect to the main tube body that is determined on the basis of where the secretions or body fluids will tend to accumulate. The specific location of the inflation conduits, likewise, can be located within the wall of the main tube body at any desired location so long as there is communication from the respective pilot balloons to the inflatable cuff and adjustment balloon. Moreover, inflation conduits could be provided internal or external of the main tube body.

It is further contemplated that the means for adjusting the free end portion of the suction tube and thus the suction opening at the end thereof can be other means than the adjustment balloon specifically described above with respect to each of the embodiments. Other mechanical or electrical devices could be used so long as the effect is to radially move the suction opening with respect to the main tube body and the body passageway to be intubated.

We claim:

1. A tubular assembly for intubation within a body passageway comprising:
   a main tube body defining a primary lumen through which fluid can pass;
   a means for holding and sealing said main tube body to the body passageway during intubation so that fluid passing into or out of the body passageway passes through said primary lumen;
   a suction tube secured to said main tube body defining between sidewalls thereof an unobstructed suction passageway, said suction tube having an adjustable free end portion not directly connected to said main tube body and movable relative thereto, said adjustable free end portion being provided with a suction opening; and
   actuating means independent of the means for holding and sealing the main tube body and located adjacent said suction opening, for selectively radially adjusting said suction opening with respect to said main tube body, said actuating means being positioned between said adjustable free end portion of said suction tube and said main tube body to move said suction opening between an innermost position adjacent said main tube body and a radially outermost position, independently of the means for holding and sealing the main tube body.

2. The assembly of claim 1, wherein said means for selectively radially adjusting said suction opening comprises an adjustment balloon connected between said main tube body and said adjustable free end portion, and fluid conduit means for providing fluid communication between said adjustment balloon and a source, said adjustment balloon being inflatable and deflatable to selectively radially adjust said adjustable free end portion.

3. The assembly of claim 2, wherein said fluid conduit means comprises a fluid conduit defined within the wall of said main tube body to pass axially through the wall, and a port through an outer surface of said main tube body that opens into said adjustment balloon.

4. The assembly of claim 3, wherein said means for holding and sealing said main tube body to the body passageway comprises an inflatable cuff positioned around said main tube body at a distal end thereof which is insertable within the body passageway, and a second fluid conduit means for providing fluid communication between said inflatable cuff and a second source.

5. The assembly of claim 4, wherein said adjustable free end portion is located further away from the distal end of said main tube body than said inflatable cuff so that said suction opening is adjustably positioned near said inflatable cuff.

6. The assembly of claim 5, wherein said suction tube provides a secondary lumen through which fluid passes, and said suction tube, in cross-section of the tubular assembly, lies external to said main tube body on the outer surface of the main tube body.

7. The assembly of claim 5, wherein said suction tube provides a secondary lumen through which fluid passes, and said suction tube, in cross-section of the tubular assembly, lies partially within said main tube body and partially external to said main tube body.

8. The assembly of claim 5, wherein said suction tube provides a secondary lumen through which fluid passes, and said suction tube, in cross-section of the tubular assembly, lies within said main tube body such that the suction tube is concealed within the main tube body.

9. An endotracheal tube for intubation within a body passageway comprising:
   a main tube body defining a primary lumen through which fluid can pass;
   a means insertable into the body passageway for holding and sealing said main tube body to the body passageway during intubation so that fluid passing into or out of the body passageway passes through said primary lumen;
   a suction tube secured to said main tube body and having an adjustable free end portion not directly connected to said main tube body and movable relative thereto, said adjustable free end portion further having a suction opening, said suction opening being positioned nearby said means for holding and sealing said main tube body to the body passageway; and
   actuating means independent of the means for holding and sealing the main tube body and located adjacent said suction opening and said means for holding and sealing said main tube body for selectively radially adjusting said suction opening with respect to said main tube body so that said suction opening can be positioned adjacent to an internal surface of the body passageway into which the intubation assembly is to be intubated, said actuating means being positioned between said adjustable free end portion of said suction tube and said main tube body to move said suction opening between an innermost position adjacent said main tube body and a radially outermost position, independently of the means for holding and sealing the main tube body.

10. The assembly of claim 9, wherein said means for selectively radially adjusting said suction opening comprises an adjustment balloon connected between said main tube body and said adjustable free end portion, and fluid conduit means for providing fluid communication between said adjustment balloon and a source, said adjustment balloon being inflatable and deflatable to selectively radially adjust said adjustable free end portion.

11. The assembly of claim 10, wherein said fluid conduit means comprises a fluid conduit defined within the wall of said main tube body to pass axially through the wall, and a port through an outer surface of said main tube body that opens into said adjustment balloon.

12. The assembly of claim 11, wherein said means for holding and sealing said main tube body to the body passageway comprises an inflatable cuff positioned around said main tube body at a distal end thereof which is insertable within the body passageway, and a second fluid conduit means for providing fluid communication between said inflatable cuff and a second source.

13. The assembly of claim 12, wherein said adjustable free end portion is located further away from the distal end of said main tube body than said inflatable cuff so that said suction opening is adjustably positioned near said inflatable cuff.

14. The assembly of claim 13, wherein said suction tube provides a secondary lumen through which fluid passes, and said suction tube, in cross-section of the tubular assembly, lies external to said main tube body on the outer surface of the main tube body.

15. The assembly of claim 13, wherein said suction tube provides a secondary lumen through which fluid passes, and said suction tube, in cross-section of the tubular assembly, lies partially within said main tube body and partially external to said main tube body.

16. The assembly of claim 13, wherein said suction tube provides a secondary lumen through which fluid passes, and said suction tube, in cross-section of the tubular assembly, lies within said main tube body such that the suction tube is concealed within the main tube body.

17. An endotracheal tube for intubation within a body passageway comprising:
a main tube body defining a primary lumen through which fluid can pass;
a means for holding and sealing said main tube body to the body passageway during intubation so that fluid passing into or out of the body passageway passes through said primary lumen, said means for holding and sealing said main tube body to the body passageway comprising an inflatable cuff positioned around said main tube body at a distal end thereof to be inserted within the body passageway when intubated, and a fluid conduit means for providing fluid communication between said inflatable cuff and a source;
a suction tube secured to said main tube body and having an adjustable free end portion not directly connected to said main tube body and movable relative thereto, said adjustable free end portion further having a suction opening, said adjustable free end portion being located with respect to said inflatable cuff further away from the distal end of said main tube body such that said suction opening is positioned nearby said inflatable cuff; and
actuating means independent of the means for holding and sealing the main tube body and located adjacent said suction opening and said means for holding said main tube body for selectively radially adjusting said suction opening with respect to said main tube body so that said suction opening can be positioned adjacent to an internal surface of the body passageway into which the intubation assembly is to be intubated, said means for selectively radially adjusting said suction opening being positioned between said adjustable free end portion of said suction tube and said main tube body to move said suction opening between an innermost position adjacent said main tube body and a radially outer-most position, independently of the means for holding and sealing the main tube body.

18. The assembly of claim 17, wherein said means for selectively radially adjusting said suction opening comprises an adjustment balloon connected between said main tube body and said adjustable free end portion, and fluid conduit means for providing fluid communication between said adjustment balloon and a source, said adjustment balloon being inflatable and deflatable to selectively radially adjust said adjustable free end portion.

19. A tubular assembly for intubation within a body passageway comprising:
a main tube body defining a primary lumen through which fluid can pass;
a means for holding and sealing said main tube body to the body passageway during intubation so that fluid passing into or out of the body passageway passes through said primary lumen;
a suction tube secured to said main tube body defining between sidewalls thereof an unobstructed suction passageway, said suction tube having an adjustable free end portion not directly connected to said main tube body and movable relative thereto, said adjustable free end portion being provided with a suction opening; and
actuating means independent of the means for holding and sealing the main tube body for selectively radially adjusting said suction opening with respect to said main tube body, said actuating means being positioned between said adjustable free end portion of said suction tube and said main tube body to move said suction opening between a radially inner-most position adjacent said main tube body and a radially outer-most position, independently of the means for holding and sealing the main tube body, and without relative axial movement of the suction tube with respect to the main tube body.

20. The assembly of claim 19, wherein said suction tube is fixed against axial movement relative to the main tube body.

21. A tubular assembly for intubation within a body passageway comprising:
a main tube body defining a primary lumen through which fluid can pass;
a means for holding and sealing said main tube body to the body passageway during intubation so that fluid passing into or out of the body passageway passes through said primary lumen;
a suction tube secured to said main tube body having an adjustable free end portion not directly connected to said main tube body and movable relative thereto, said adjustable free end portion provided with a suction opening; and
means for selectively radially adjusting said suction opening with respect to said main tube body;
wherein:
said means for selectively radially adjusting said suction opening is positioned between said adjustable free end portion of said suction tube and said main tube body to move said suction opening from an innermost position adjacent said main tube body to a radially outermost position;
said means for selectively radially adjusting said suction opening comprises an adjustment balloon connected between said main tube body and said adjustable free end portion, and fluid conduit means for providing fluid communication between said adjustment balloon and a source, said adjustment balloon being inflatable and deflatable to selectively radially adjust said adjustable free end portion;

said fluid conduit means comprises a fluid conduit defined within the wall of said main tube body to pass axially through the wall, and a port through an outer surface of said main tube body that opens into said adjustment balloon; and said means for holding and sealing said main tube body to the body passageway comprises an inflatable cuff positioned around said main tube body at a distal end thereof which is insertable within the body passageway, and a second fluid conduit means for providing fluid communication between said inflatable cuff and a second source.

22. An endotracheal tube for intubation within a body passageway comprising:

a main tube body defining a primary lumen through which fluid can pass;

a means for holding and sealing said main tube body to the body passageway during intubation so that fluid passing into or out of the body passageway passes through said primary lumen;

a suction tube secured to said main tube body having an adjustable free end portion not directly connected to said main tube body and movable relative thereto, said adjustable free end portion further having a suction opening, said suction opening being positioned nearby said means for holding and sealing said main tube body to the body passageway; and means for selectively radially adjusting said suction opening with respect to said main tube body so that said suction opening can be positioned adjacent to an internal surface of the body passageway into which the intubation assembly is to be intubated; wherein:

said means for selectively radially adjusting said suction opening is positioned between said adjustable free end portion of said suction tube and said main tube body to move said suction opening from an innermost position adjacent said main tube body to a radially outermost position;

said means for selectively radially adjusting said suction opening comprises an adjustment balloon connected between said main tube body and said adjustable free end portion, and fluid conduit means for providing fluid communication between said adjustment balloon and a source, said adjustment balloon being inflatable and deflatable to selectively radially adjust said adjustable free end portion;

said fluid conduit means comprises a fluid conduit defined within the wall of said main tube body to pass axially through the wall, and a port through an outer surface of said main tube that opens into said adjustment balloon; and said means for holding and sealing said main tube body to the body passageway comprises an inflatable cuff positioned around said main tube body at a distal end thereof which is insertable within the body passageway, and a second fluid conduit means for providing fluid communication between said inflatable cuff and a second source.

23. An endotracheal tube for intubation within a body passageway comprising:

a main tube body defining a primary lumen through which fluid can pass;

a means for holding and sealing said main tube body to the body passageway during intubation so that fluid passing into or out of the body passageway passes through said primary lumen, said means for holding and sealing said main tube body to the body passageway comprising an inflatable cuff positioned around said main tube body at a distal end thereof to be inserted within the body passageway when intubated, and a fluid conduit means for providing fluid communication between said inflatable cuff and a source;

a suction tube secured to said main tube body having an adjustable free end portion not directly connected to said main tube body and movable relative thereto, said adjustable free end portion further having a suction opening, said adjustable free end portion being located with respect to said main tube body further away from the distal end of said main tube body such that said suction opening is positioned nearby said inflatable cuff; and means for selectively radially adjusting said suction opening with respect to said main tube body so that said suction opening can be positioned adjacent to an internal surface of the body passageway into which the intubation assembly is to be intubated;

wherein said means for selectively radially adjusting said suction opening comprises an adjustment balloon connected between said main tube body and said adjustable free end portion, and fluid conduit means for providing fluid communication between said adjustment balloon and a source, said adjustment balloon being inflatable and deflatable to selectively radially adjust said adjustable free end portion.

* * * * *